(12) United States Patent
Poole

(10) Patent No.: US 7,618,385 B2
(45) Date of Patent: Nov. 17, 2009

(54) HEAD SUPPORT

(76) Inventor: Darrell Maitland Poole, Suite 78, 47 High Street, Auckland (NZ)

( * ) Notice: Subject to any disclaimer, the term of this patent is extended or adjusted under 35 U.S.C. 154(b) by 610 days.

(21) Appl. No.: 11/152,784

(22) Filed: Jun. 15, 2005

(65) Prior Publication Data

US 2005/0283884 A1 Dec. 29, 2005

Related U.S. Application Data

(63) Continuation-in-part of application No. 10/217,164, filed on Aug. 13, 2002, now abandoned, which is a continuation of application No. 09/737,557, filed on Dec. 18, 2000, now abandoned.

(51) Int. Cl.
*A61F 5/00* (2006.01)
(52) U.S. Cl. .................. 602/17; 602/18; 128/DIG. 23
(58) Field of Classification Search ............... 602/5, 602/17, 18, 19; 128/DIG. 23
See application file for complete search history.

(56) References Cited

U.S. PATENT DOCUMENTS

| 2,223,276 | A | * | 11/1940 | Ward | 602/18 |
| 4,628,913 | A | * | 12/1986 | Lerman | 602/18 |
| 5,531,669 | A | * | 7/1996 | Varnau | 602/18 |
| 5,865,773 | A | * | 2/1999 | Koledin | 602/18 |
| 6,267,741 | B1 | * | 7/2001 | Lerman | 602/18 |

* cited by examiner

*Primary Examiner*—Michael A. Brown
(74) *Attorney, Agent, or Firm*—Jacobson Holman PLLC

(57) ABSTRACT

The invention relates to head or neck supports which support the head or neck in a tilted back position and comprises or includes:
a) a harness locatable to the upper body portions of a person,
b) a rigid member extending from a region of the harness stabilized in respect of and by the use of the harness relative to the body, and when in use, the harness is attached to the body of a person, the rigid member extending therefrom to provide a support region thereof which when the person is in a substantially upright position, and the head is tilted backwards to allow viewing of an object above the horizontal, the support region comes in contact with at least part of the back of the head and provides at least vertical support to the head.

34 Claims, 9 Drawing Sheets

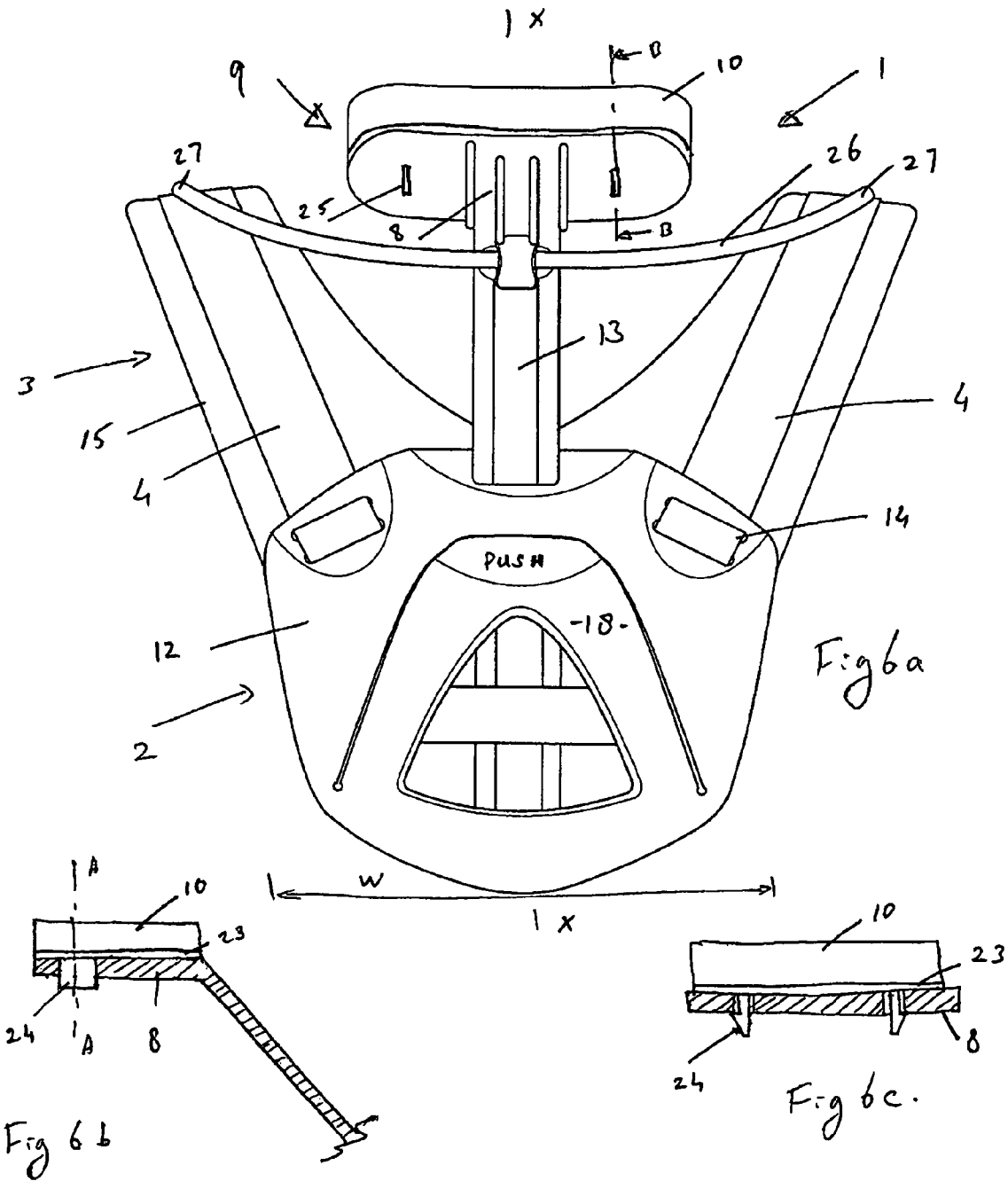

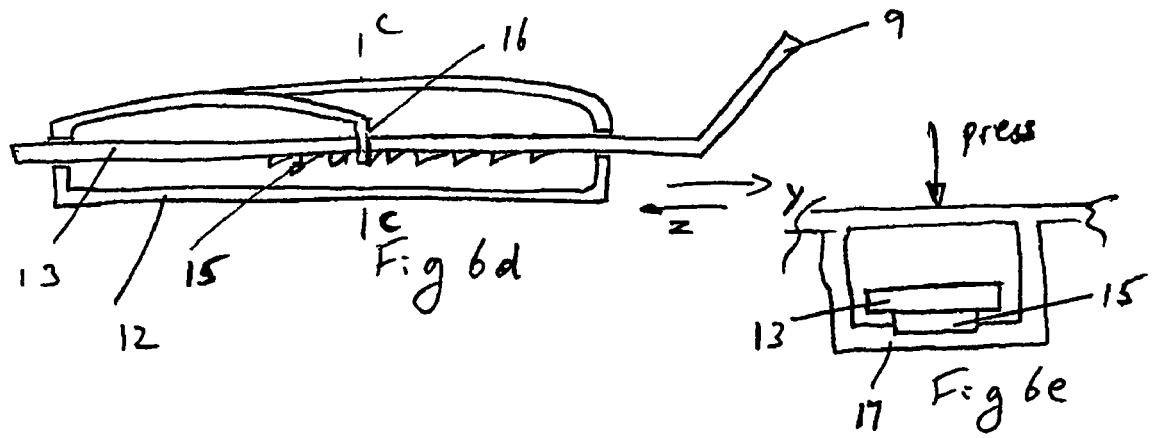
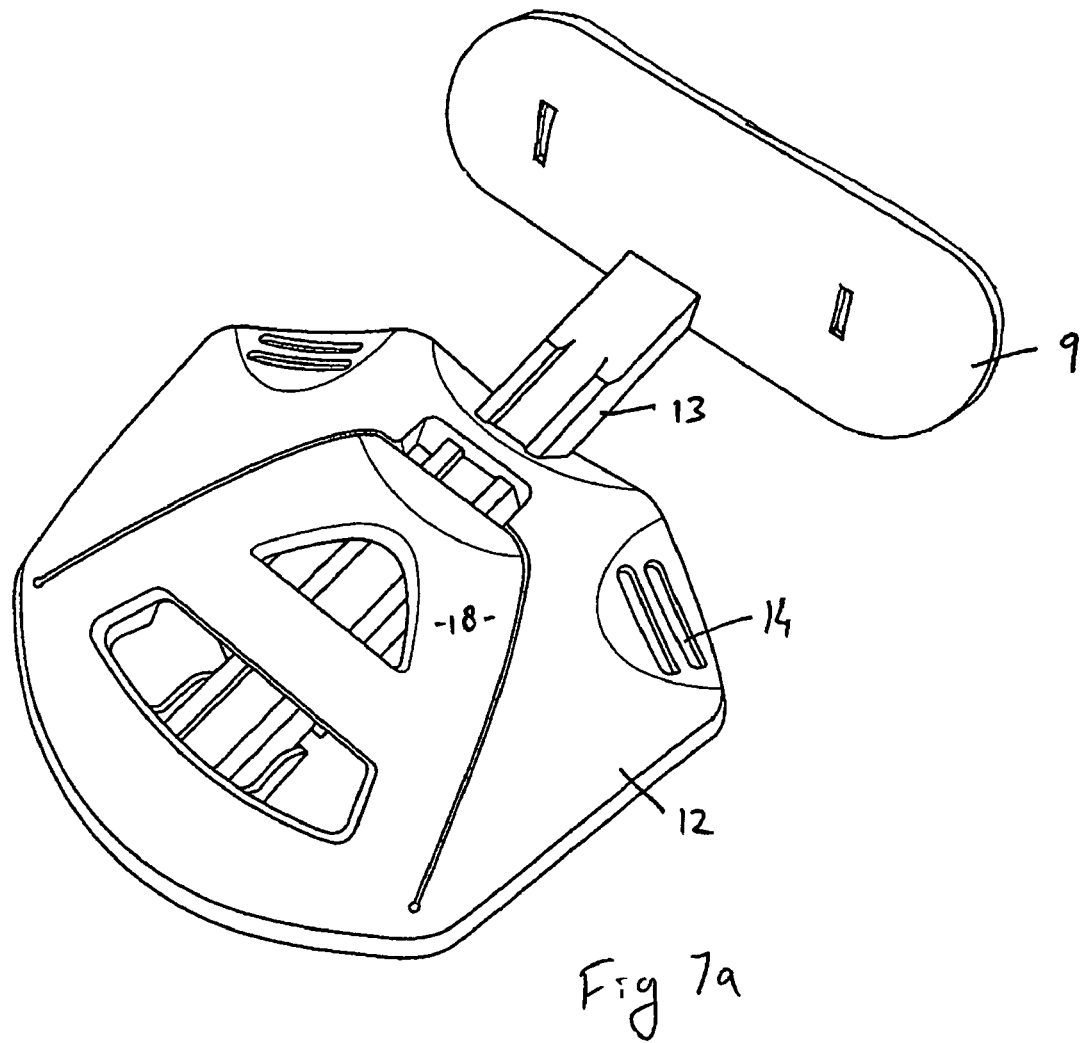

NECK BRACE/HARNESS/USER

NECK BRACE/BACKPACK/USER

NECK BRACE/BACKPACK

NECK BRACE/HARNESS/USER

HEAD SUPPORT

This is a continuation in-part of U.S. patent application Ser. No. 10/217,164, filed Aug. 13, 2002, now abandoned which in turn is a continuation of U.S. patent application Ser. No. 09/737,557, filed Dec. 18, 2000, now abandoned which in turn is a nationalization of PCT/NZ00/00106 filed Jun. 21, 2000.

FIELD OF THE INVENTION

The present invention relates to improvements in or relating to head supports. More particularly but not exclusively it relates to head or neck supports which support the head or neck in a tilted back position to provide support to the head for facilitating the viewing of objects overhead.

BACKGROUND OF THE INVENTION

In activities such as climbing, fruit picking, plastering, painting or attending air shows or the like, a person may, for long durations, have his/her head tilted back to allow them to look upwardly. Such tilting of the head can only be sustained comfortably, for a limited period of time. Although muscle strength to support a head in a tilted position does vary from person to person, after a while anyone will start to feel the strain in having to maintain the head in such a condition. In activities such as climbing where a belayer is positioned below the climber and whose object is to prevent too much slack in the rope which is attached to the climber, it is essential that this person keeps a close eye on the progress of the climber as he/she ascends or descends. Failure to maintain a substantially constant eye on the progress of the climber could result in a sufficient amount of slack in the rope which, if the climber falls, could result in injury or death.

Furthermore in some vocations such as in plastering or fruit picking a person may also be in a position where the head of a person is constantly tilted back. This can place significant strain on the muscles or neck of the person and can cause future back problems.

It is an object of the present invention to provide a head support which will at least go some way towards providing a means of supporting the head or neck of a person in a tilt back condition which is capable of having some degree of flexibility to allow varying angles of inclination of the head of a person to be supported or which will at least provide the public with a useful choice.

As used herein, "the horizontal" describes that field of view of the eyes in the plane substantially perpendicular to the body of the user, which is considered as being in the "upright" position. The "upright" position may include a position which is not strictly vertical or upright as in conventionally understood. For example, when in a standing, leaning back, or sitting position, the body is defined as being in the "upright" position. The "horizontal" view is that with the eyes facing substantially straight ahead. In viewing an object "above the horizontal" the head and/or neck will require tilting backwards somewhat from this position.

"Harness" as used herein may also include a backpack or other system capable of being worn by or attached to a user, and supporting or appending to or functioning as a head or neck support as described.

SUMMARY OF THE INVENTION

In a first aspect the present invention consists a head support comprising or including:

a) a harness locatable to the upper body portions of a person, b) a rigid member extending from a region of said harness stabilized in respect of and by the use of the harness relative to the body wherein, when in use and said harness is attached to the body of a person, said rigid member extends from the harness to provide a support region thereof which when said person is in a substantially upright position, and their head is tilted backwards to allow viewing of an object above the horizontal, said support region comes in contact with at least part of the back of the head and provides at least vertical support to the head.

Preferably said rigid member is or includes an elongate member having a vertically extending portion which, in use, extends substantially parallel with the spine of a user, and an outwardly projecting portion which extend in use, away from said vertically extending portion, outwardly from the body of a user, wherein at said outwardly projecting portion or near the distal end thereof, said support region is provided.

Preferably said vertically extending portion is engaged to said harness.

Preferably said rigid member includes lateral extension, extending each side from said vertically extending portion of said rigid member, said lateral extension having at its laterally outward portions, a shoulder strap engaging means to allow the location of shoulder straps of said harness with said lateral extension.

Preferably said lateral extension is a base member.

Preferably said rigid member comprises a base member from which said elongate member projects, said elongate member engaged to said base member in a manner capable (a) to, in one condition of said rigid member, be displaceable relative to said base member to allow the movement of said support means in a direction along the longitudinal direction of said elongate member and (b) to, in a second condition of said rigid member, be selectively restrained from said movement relative to said base member by a securing means.

Preferably said elongate member is captured for sliding engagement to said base member to allow displacement of said elongate member relative to said base member in a direction along the longitudinal direction of said elongate member.

Preferably said securing means in an indexed securing means allowing retaining of said movement when said base member and said elongate member are at at least two relative dispositions to each other.

Preferably said securing means is defined by cooperative indexing elements of said elongate member and said base member.

Preferably said cooperative indexing elements comprise of an index (preferably ratchet) surface and pawl, said index surface being part of one of said elongate element and said base element, and said pawl being part of the other of said elongate elements and said base.

Preferably said pawl can be selectively moved to a position where it is in a non operative association with said index surface to allow an unfettered movement of said elongate member with said base member.

Preferably said pawl is mounted in a manner biased towards a condition where it is in operative association with said index surface yet movable by a user to said position where it is in non operative association.

Preferably said index surface is a ratchet surface comprising an array of saw tooth like projections.

Preferably said saw tooth like projections are presented in a manner to, when said pawl is in operative association, allow the movement of said elongate member in only one direction relative to said base member.

Preferably said securing means is a quick release clamp provided by said base member and in clampable engagement with said elongate member.

Preferably said rigid member comprises a base member from which said elongate member projects, said elongate member engaged, in a moveable manner in a direction along the longitudinal direction of said elongate member, to said base member and restainable from movement in at least a direction wherein said support region displaces towards said base member, by a securing means.

Preferably said support region is formed or shaped to additionally provide support to the sides of the head.

Preferably the head support includes one or more adjustment device selected from:
(i) an adjustment device capable of altering a tilt of said support region;
(ii) an adjustment device capable of altering a height of the support region with respect to the harness;
(iii) an adjustment device capable of altering a distance between said rigid member and said back of said user.

Preferably said support region includes padding to, in use, be rested on by the head of the user.

Preferably said padding is provided by a removable pad, selectively fastenable to the support region.

Preferably said support region includes a cover to present a surface onto which the head of the user can rest.

Preferably said cover is a removable (preferably disposable) cover.

Preferably said support region is presented to receive a head contact pad in a releasably fastenable manner, to hold said head contact pad in a position to allow it to engage with the head of the user.

Preferably said rigid member includes at least one bracing member extending between said rigid member at or proximate said support region and said harness to, in use, brace said support region against movement thereof in a direction away from the body of the user.

Preferably said rigid member includes two bracing members, each bracing member extending from said elongate member to an anterior more to be disposed portion of said harness, each bracing member projecting from a respective side of said elongate member.

Preferably said harness includes over shoulders straps and each said bracing member is engaged to a respective over the shoulder strap.

Preferably said bracing members can be adjusted to hold said elongate member in different anterior/posterior direction positions elative to the body, when in use.

Preferably said bracing members include length adjustment elements to allow said bracing members to be adjusted.

Preferably each said bracing members and/or said harness include a plurality of anchor points for the engagement of said bracing element with said harness to allow said bracing members to be adjusted.

Preferably said bracing elements are engaged to said elongate member at or proximate said support region.

Preferably said harness includes over the shoulder straps and a chest strap engaged to said over the shoulder straps to be locatable about the chest of a wearer at or immediately below or adjacent the pectorals of a wearer.

Preferably said harness includes over the shoulder straps and a strap extending between the shoulder straps at the chest to be located region a wearer to restrain the over the shoulder straps from separating.

In a second aspect the present invention consists in a head support comprising
a backpack
a rigid member having a vertically extending region and an outwardly extending region supporting the head, when in use in respect of the vertically upright body of a user, in a tilted backwards position to allow head supported viewing of an object above the horizontal, wherein said vertically extending member has a region engaging with a head support receiving device located at least adjacent a top of the back pack.

In a further aspect the present invention consists in a head support comprising or including:
a) a harness locatable to the upper body portions of a person,
b) a rigid member extending from a region of said harness stabilized in respect of and by the use of the harness relative to the body wherein, when in use, said harness is attached to the body of a person, said rigid member extending from the harness to provide a support region thereof which when said person is in a substantially upright position, and the head is tilted backwards to allow viewing of an object above the horizontal, said support region comes in contact with at least part of the back of the head and provides at least vertical support to the head, said rigid member being or including an elongate member having a vertically extending portion which, in use, extends substantially parallel with the spine of a user, and an outwardly projecting portion which extend in use, away from said vertically extending portion, outwardly from the body of a user, wherein at said outwardly projecting portion or near the distal end thereof, said head support region is provided.

In a further aspect the present invention consists in a head support comprising or including:
a) a harness locatable to the upper body portions of a person
b) a rigid member extending from a region of said harness stabilised in respect of and by the use of the harness relative to the body wherein, when in use, said harness is attached to the body of a person, said rigid member extending therefrom to provide a support region thereof which when said person is in a substantially upright position, and the head is tilted backwards to allow viewing of an object above the horizontal, said support region comes in contact with at least part of the back of the head and provides at least vertical support to the head.

Preferably said rigid member has a vertically extending portion which, in use extends substantially vertically and parallel with the general upright position of said user, and an outwardly extending portion which extends, in use from said vertically extending portion, outwardly from the body of a user wherein at or near the distal end of said outwardly extending portion said head supporting region is provided.

Preferably said rigid member is secured to said harness at said vertically extending portion thereof.

Preferably said rigid member is provided with padding in those regions which, when said head support is in use, is in contact with the body of the user.

Preferably said harness is secured to the vertically extending portion of said rigid member to, when said harness is secured to the body of the user, press said rigid means against the back of the user, more preferably said rigid member is pressed against is the upper spine region of the back of the user.

Alternatively said rigid member is held apart from the upper spine region of the back of the user, preferably by means of a strut or brace attached to said harness; more preferably the rigid member is not in contact with the upper spine region of the back of the user.

Preferably said rigid member is an elongate member having a first distal end defining the lower end of the substantially vertical member and a second distal end defining the outer end region of said outwardly extending portion thereof.

Preferably said rigid member is an extrusion, preferably plastics, or is of an elongate sheet material shaped, moulded or fabricated to provide said vertically extending region and said outwardly extending region thereof.

Preferably said head supporting region is formed or shaped to additionally provide support to the sides of the head.

Preferably said harness includes or comprises at least two shoulder engaging straps, one each to locate over a shoulder of the user and to locate with said rigid means, or an extension thereof, at the back of said user.

Preferably said shoulder straps are each endless members in use and have a means to open such as a buckle and also to provide an adjustment in the length of said strap.

Preferably said rigid member is provided with lateral extensions, extending from said vertically extending portion of said rigid member from each side thereof each said lateral member having at its distal end thereof a shoulder strap engaging means to allow the location of said shoulder strap with said lateral member.

Preferably each lateral member allows the longitudinal sliding engagement of each shoulder strap at its distal ends thereof, to provide, when said harness is in use a directional stability of said second distal end of said substantially vertical member to prevent it from moving to any significant and functionless degree in a substantially horizontal direction in respect of the head.

Preferably the shoulder strap means each locate to said rigid means at the distal end of said vertically extending member thereof.

Preferably said harness further includes a chest or waist encompassing strap which is located at substantially the point where said shoulder straps locate at said rigid means, and is preferably provided with a release buckle and adjustable means, about the waist or chest of the user.

Preferably the head support is a recreational head support.

Alternatively the head support is for vocational use.

Preferably the head support includes adjustment means capable of altering the tilt of said member, and/or of said second distal end of said substantially vertical member relative to said first distal end.

Preferably the head support includes adjustment means capable of altering the height of the rigid member with respect to the harness, and/or the head support region with respect to the rigid member and/or the harness.

Preferably the head support includes adjustment means capable of altering the distance between said rigid member and said back of said user.

In a further aspect the present invention consists in a head support comprising a rigid member having a vertically extending region and an outwardly extending region supporting the head, when in use in respect of the vertically upright body of a user, in a tilted backwards position to allow viewing of an object above the horizontal, wherein said vertically extending member has a region adapted for engaging with a head support receiving means located at/or near the top of a back pack.

Preferably the head support includes adjustment means capable of altering the tilt of said member, and/or of said second distal end of said substantially vertical member relative to said first distal end.

Preferably the head support includes adjustment means capable of altering the height of the rigid member with respect to the harness, and/or the head support region with respect to the rigid member and/or the harness.

Preferably the head support includes adjustment means capable of altering the distance between said rigid member and said back of said user.

Preferably the head support is a recreational head support.

Alternatively the head support is for vocational use.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples.

BRIEF DESCRIPTION OF THE DRAWINGS

One preferred form of the present invention will now be described with reference to the accompanying drawings in which:

FIG. 6A is a back view of an alternative form of the head support of the present invention, FIG. 6B is a sectional view through section BB of FIG. 6A, FIG. 6C is a sectional view at section AA of FIG. 6B, FIG. 6D is a sectional view along part of the base pad 12 and head rest carrying member 13 parallel to axis XX, FIG. 6E is a sectional view through section CC of FIG. 6D, FIG. 7A is a perspective view of the rigid member of the present invention for engagement with a body harness.

DETAILED DESCRIPTION OF THE INVENTION

Figure 1:
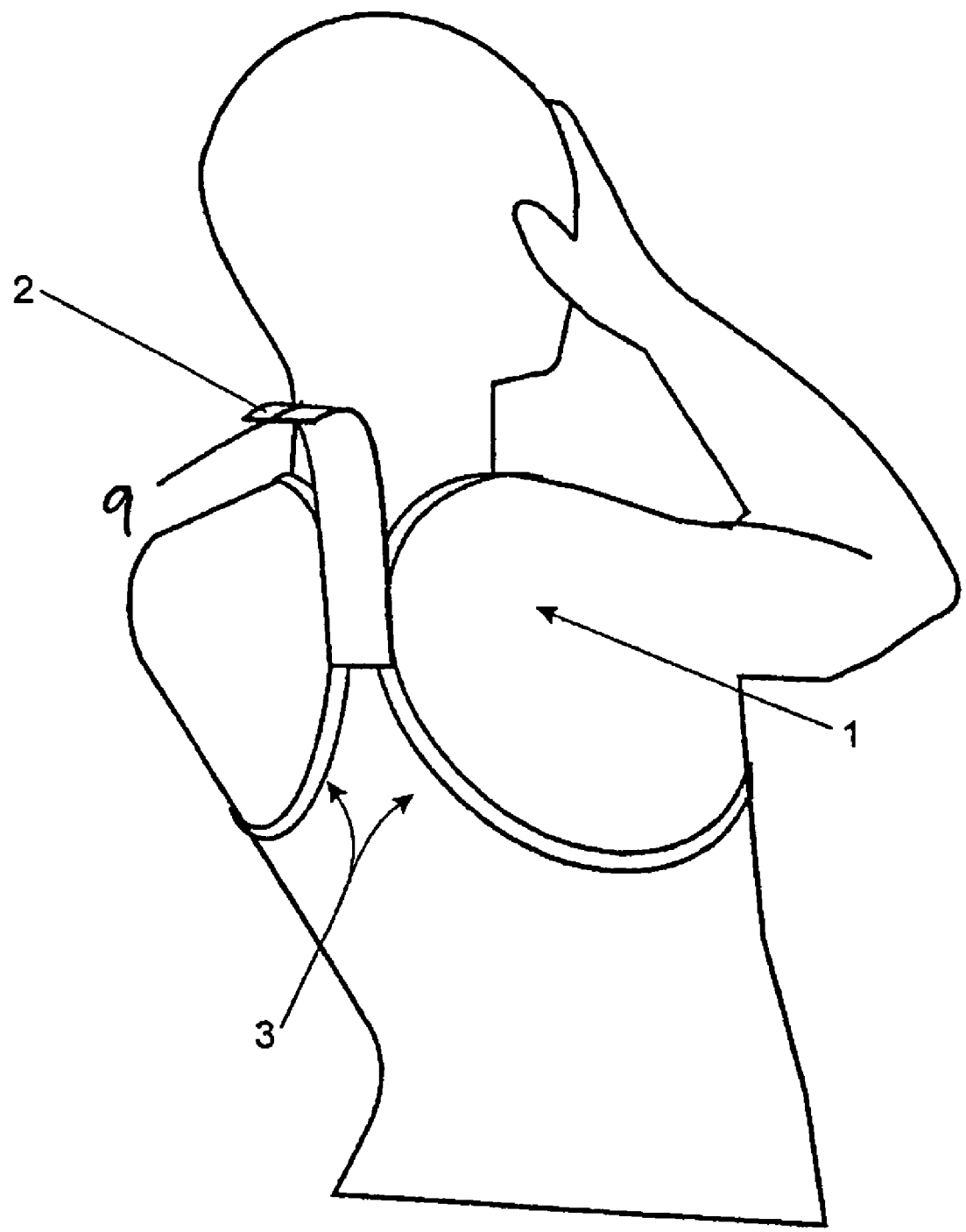
FIG. 1 is a perspective view of the back of a user of the present invention illustrating the head support located with the user in the preferred condition.

With reference to FIG. 1 there is shown a head support 1 which consists of a rigid member 2 and a harness 3 located or secured with said rigid member 2.

The rigid member 2 and harness 3 are adapted to be located to the user of the head support 1 such that when the user is standing upright and tilts his/her head backwards, there is a head rest region 9 of said rigid member 2 with which the tilted back head can contact and be provided with a vertical support thereby. It is to be noted that the head support 1 of the present invention may simply provide neck support for viewing above the horizontal rather than full vertical head support, without departing from the scope of some of the aspects of the present invention described in the specification. With reference to FIGS. 2, 9, 10 and 11 there is shown a user of the head support 1 with his head tilted backwards and a part of the head locating against a portion of the rigid member 2 to provide the user with a comfortable and vertical support for the head and/or neck.

Figure 2:
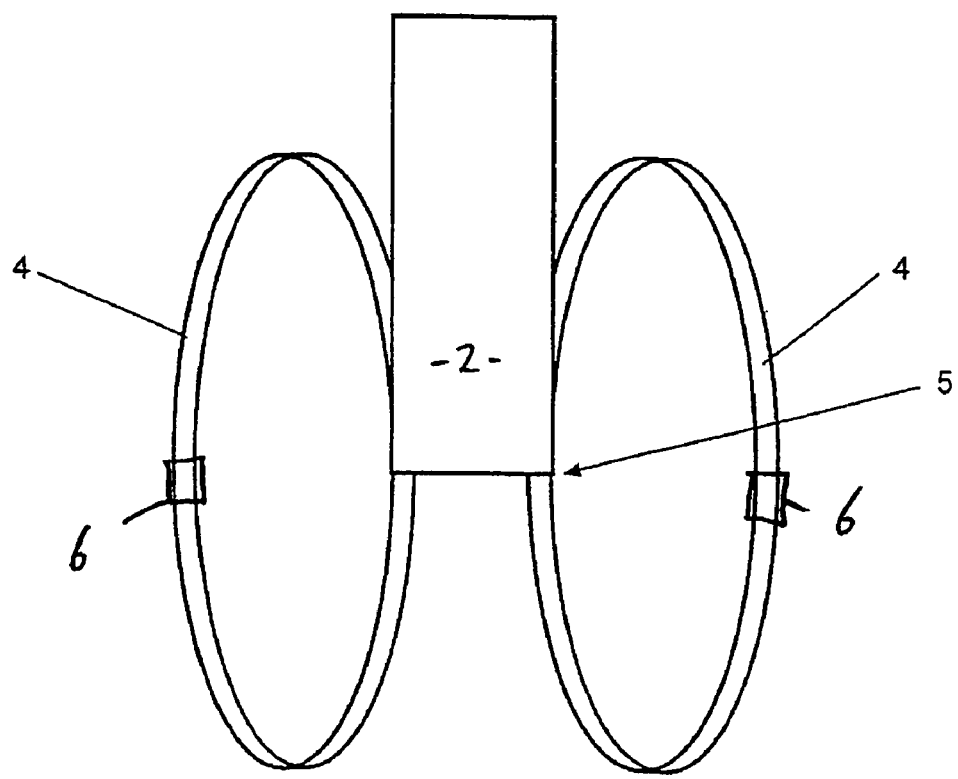
FIG. 2 is a front view in direction AA of FIG. 3 of the head support of the present invention.
Figure 3:
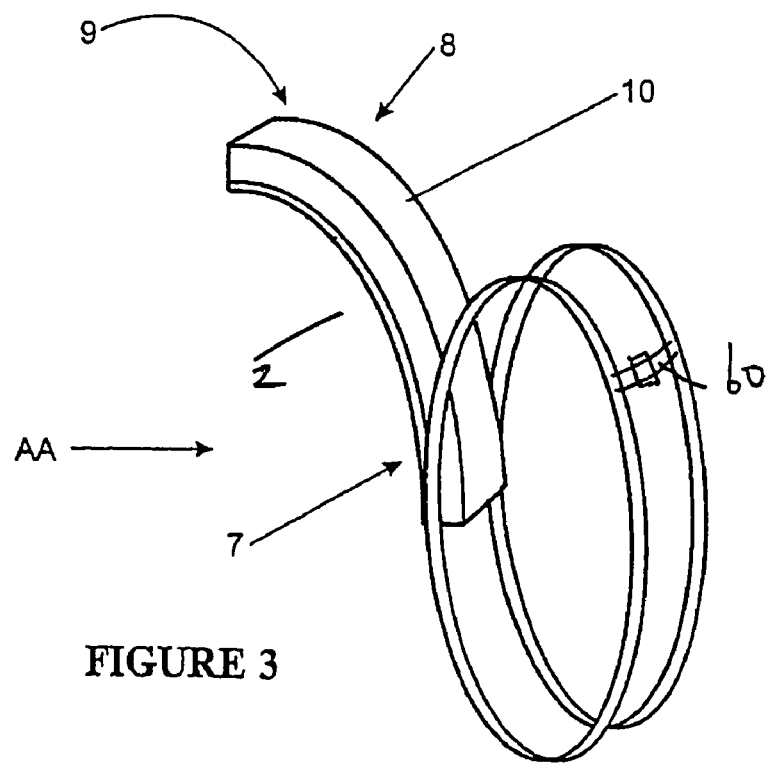
FIG. 3 is a perspective view of the head support as shown in FIG. 2.

In reference to FIGS. 2 and 3 one form includes a harness 3 which is locatable about the upper body regions of a user of the present invention. The harness 3 is of a configuration which can provide at least vertical stability to the rigid member 2. It is to be noted that the "harness" can also include a backpack without departing from the scope of the invention.

In FIG. 2 there is shown a harness 3 which consists of two shoulder straps 4 which are locatable over the shoulder and underneath the armpits to return back to a region of attachment 5 between the rigid member 2 and the harness 3. The region of attachment is at or towards a lower distal end of the rigid member 2. With reference to FIG. 1 there is illustrated the shoulder straps 4 running from the region of attachment 5 to the rigid member 2, over the shoulders under the arms and back towards the region of securement. It will be appreciated by a person skilled in the art that such shoulder straps 4 may be provided with buckles and/or adjustment means 6 to allow for the head support to be reconfigured relative to the body of the user or to allow users of different body shapes and sizes to use the particular head support. Furthermore, as discussed the shoulder straps 4 may be those of a backpack.

As indicated in FIGS. 2, 3, 6 and 7 the rigid member 2 is preferably made from a sheet material such as a moulded plastic, composite or metallic or non-metallic material. The rigid member 2 preferably consists of a vertically extending region 7 and an outwardly extending region 8. The vertically extending region 7 is provided and adapted in association with the harness 3 to lie parallel to and in engagement with the back of a user of the head support 1. Preferably the vertically extending region 7 is of sufficient length to be pressed (when said harness is engaged to the user), against the back of the user to provide some stable support in respect of the user.

Figure 4:
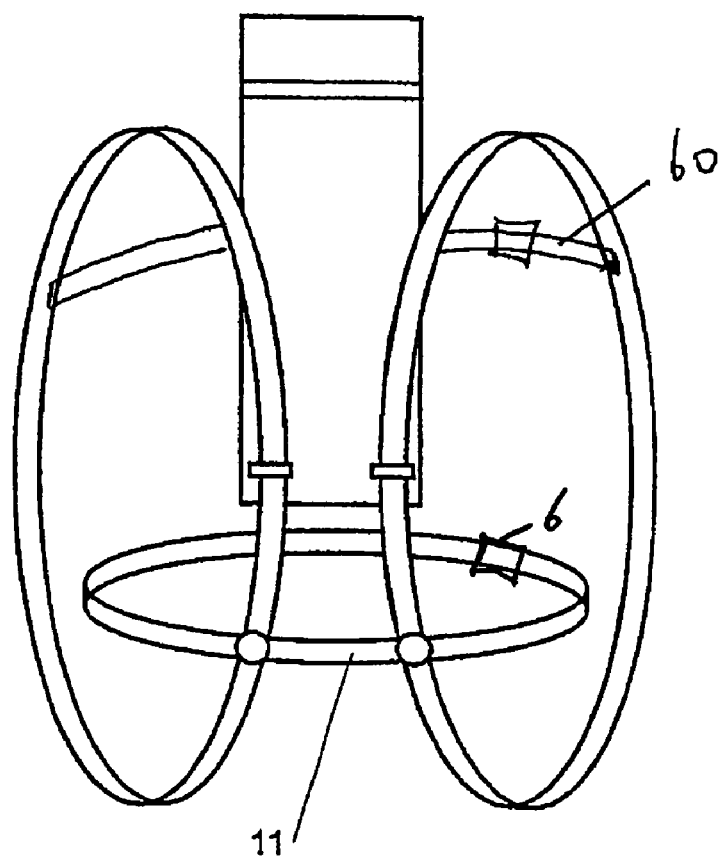
FIG. 4 is a view from the back of an alternative form of the head support of the present invention.

The outwardly extending portion 8 of the rigid member 2 has a head rest 9 with which, when said head support 1 is in use, the tilted back head of a user can comfortably located. As indicated in FIGS. 6 and 7, the outwardly extending portion 8 may be concave to allow engagement of the head as shown in FIGS. 3 and 4. For comfort in the wearing of the head support 1 there is preferably provided a padded surface 10 on that side of the rigid member 2 which is to be in contact with the body of the user.

FIG. 4 shows an alternative configuration or an additional configuration to the harness 3. To encourage the rigid means 2 to remain in stable and close contact with the back of a user a further portion of the harness 3 is provided to encompass the chest or waist of the user of the device. This chest band 11 may be attached to the shoulder straps 4 and/or be attached to the rigid member 2. This chest band 11 may be provided with a buckle 6 and/or strap length adjusting means to allow a particular head support of the present invention to be adapted for use by different sized and shaped people. The harness preferably also includes a chest tie 60 which extends between the shoulder straps 4 across the chest region. The chest tie may be a webbing which includes an adjustment buckle to allow for the chest tie to be adjusted in length. The chest tie 60 allows for the shoulder straps to be drawn together and held together by the chest tie. This can be advantageous in providing more comfort to the wearer to prevent the shoulder straps from sitting with too much separation across the chest. This harness configuration or any harness configuration as shown herein may have application to alternative variations of the device as herein defined.

Figure 5:
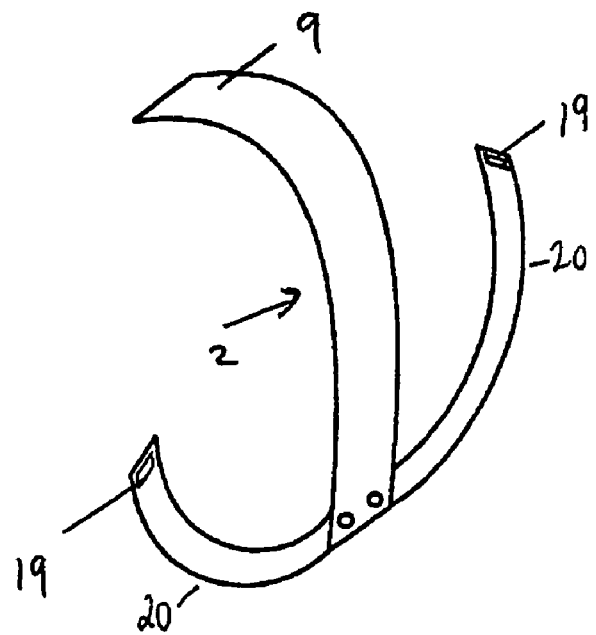
FIG. 5 illustrates the rigid member of the head support in association with a lateral stabilising means with which the straps of the harness can locate.

For further support to the rigid means 2 of the present invention a lateral stabilizer may be rigidly attached or form part of the rigid member 2. With reference to FIG. 5 such a lateral stabilizer may for example be arms 20 which extend outwardly (and preferably upwardly) from a region of the rigid member 2. Preferably the region from which the lateral stabilizers 20 extend is a lower or lower most region of the rigid member 2. The lateral stabilizers 20 are preferably made of a material similar to that of the rigid member 2 or may alternatively be made from any other material and which although preferably deformable, does have its own inherent rigidity. In the preferred form the lateral stabilizers locate at the distal ends with the shoulder straps 4. The shoulder straps will tend to draw the lateral stabilizer to conform with the upper back and shoulder shape of the user of the present invention and hence in the preferred form such lateral stabilizers 20 are of a sheet material or strip wherein the plane of the sheet or strip is in a general parallel direction with the back of the user. Such an orientation of the plane of the lateral stabilizers will allow for it to be conformed or at least in part contoured with the back of the user.

Preferably at the distal ends of the lateral stabilizer there is the provision of the slot 19 through which the shoulder straps 4 can extend while still allowing the distal ends of the lateral stabilizers 20 to have some association with said shoulder straps 4.

Figure 12:
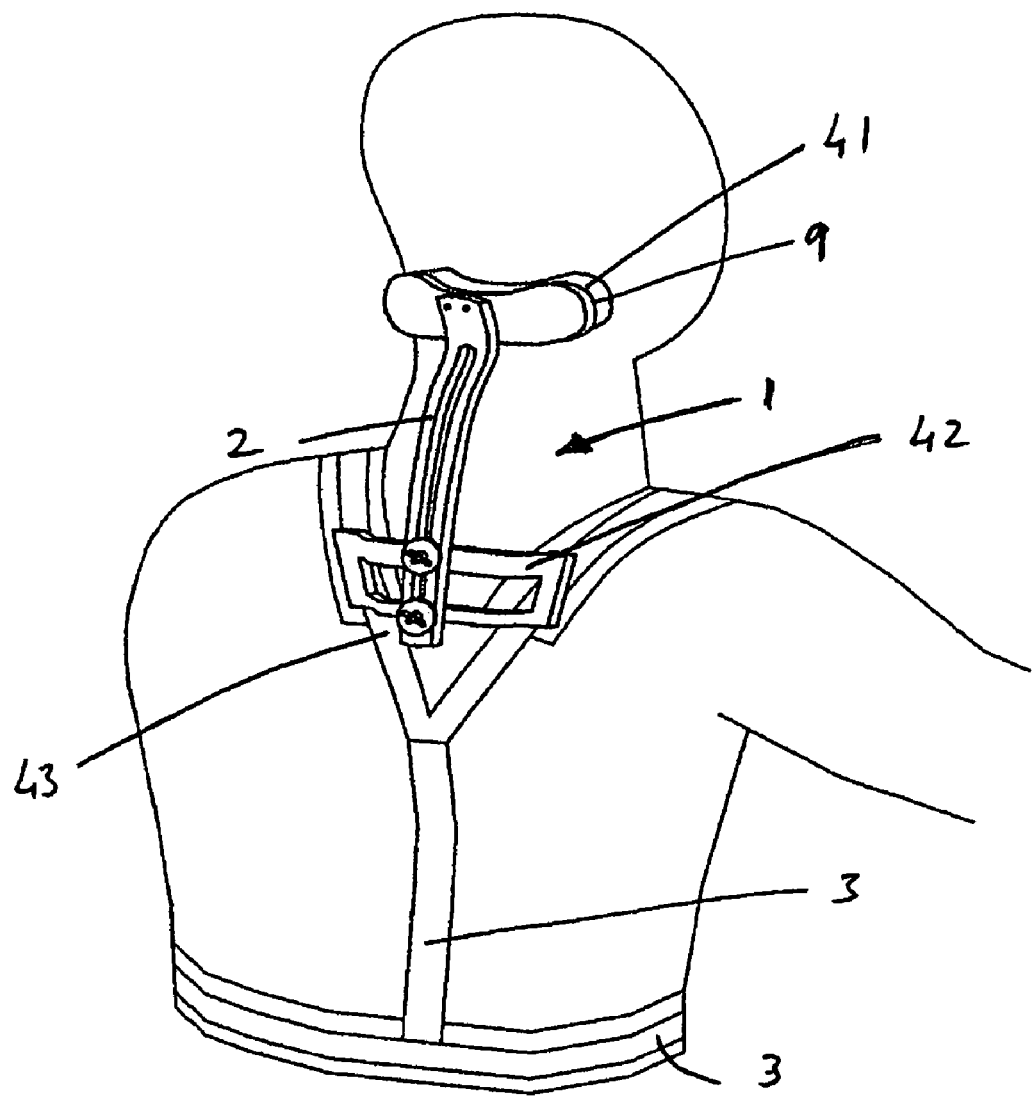
FIG. 12 illustrates the invention according to a further form.

FIG. 12 illustrates an alternative embodiment of the invention. Shown is the head support 1 which includes the rigid member 2, and the shoulder straps 4 of the harness. In this embodiment the head support 1 includes a head rest 9 preferably of a substantially arcuate form, providing further support towards the sides of the head of the user and not just the back of the head. The head support 9 also includes a padded surface 41 for comfort.

FIG. 12 further illustrates the use of a support or strut 42 as an extension of the rigid member 2 which holds and retains the rigid member 2 at a distance from the back of the user. In some situations (such as on medical or particularly orthopaedic advice) it may be preferable for the rigid member 2 to have no contact with the user's back. This embodiment is appropriate for such situations.

FIG. 12 also illustrates additional adjustment means 43 which may be employed to raise and lower the head rest 9 with respect to the head of the user. It is envisaged that a number of adjustment means may be employed individually or in combination in an embodiment according to the invention, without departing from the scope of the invention. Such adjustment means may be used to raise and lower the head rest to alter the position of the head supporting region (in respect of height, and tilt for example).

With reference to FIG. 6A there is shown a head support 1 which includes a rigid member 2. In this example the rigid member 2 consists of a base portion or base pad 12 which has an extensile head rest carrying member 13. The base pad 12 includes engagement regions 14 which allow for shoulder straps 4 to engage therewith. Similar engagement regions may be provided to allow for a chest band to engage with the base pad 12 directly or to the shoulder straps. The shoulder straps 4 may be engaged to further padding 15 forming part of the harness 3. The base pad 12 is preferably of a width (w) of at least 10 centimeters and preferably approximately 15-20 centimeters. Such a substantial width for the base pad 12 helps for the rigid member 2 to gain stability from the back of a user. The base pad 12 can be pressed against the back of a user to obtain stability thereby reducing the possibility of rotation about the axis XX of the rigid member 2. Provided to the body contactable side (opposite to the body contactable side as shown facing in FIG. 6A) may be padding which allows for the base pad 12 to sit comfortably against the back of a user. The base pad 12 is preferably located by the harness 3 to be located at the upper back portion of the user. The base pad 12 preferably sits at the shoulder blade height of a wearer. The base pad preferably does not sit at the small of the back or at the base of the back but is presented for use at a much more elevated location on the body of a wearer. In the most preferred form the base pad is of a shape so as to straddle the spine. As such in the preferred form the base pad on the body proximate more side, is of a concave profile so as to accommodate the spine within the concave without the base pad engaging or pressing unduly onto the spine of the wearer.

The base pad 12 provides support to the head rest carrying member 13. The head rest carrying member 13 is in a movable disposition relative to the base pad 12. In the most preferred form the head rest carrying member 13 is in a sliding engagement with the base pad 12. Such sliding engagement allows for the head rest carrying member 13 to move in a direction parallel to its longitudinal direction along or parallel axis XX. A slot or slots provided in the base pad 12 which are of a complimentary shape to at least part of a constant cross sectional shaped region of the head rest carrying member 13 allows for the head rest carrying member to slide along or parallel to the direction XX relative to the base pad 12. The ability for the head rest carrying member 13 to move relative to the base pad 12 allows for the head rest 9 to be varied in height. The head rest 9 in this example is carried at the distal end of the head rest carrying member 13 and is presented to be engaged by the head of a user.

To allow for convenient adjustment of the height of the head rest 9 to occur as a consequence of the movement of the head rest carrying member 13, a ratchet like relationship is established between the base pad 12 and the head rest carrying member 13.

The ratchet arrangement consists of a ratchet surface 15 provided by the head rest carrying member 13. The ratchet surface consists of a plurality of ratchet teeth which are ramped in one direction and are bluff in respect to the opposite direction (i.e. a saw tooth like configuration). A pawl 16 is provided carried by the base pad 12. The pawl has a region 17 which can interact with the teeth of the ratchet surface 15. This is for example shown in FIG. 6E where the pawl is in engagement with a bluff face of a ratchet tooth of the ratchet surface 15. The pawl 17 is carried by a resiliently displaceable zone 18 of the base pad 12. The resiliently flexible zone 18 of the base pad 12 allows for the pawl to move. Such movement is in a direction to allow for the pawl to become disengaged from the ratchet surface 15. A push or pressing on the appropriate portion of the zone 18 allows for the pawl 17 to displace away from the ratchet surface 15 thereby allowing the unfettered movement of the head rest carrying member 13. The head rest carrying member 13 when the pawl has been displaced by pushing the zone 18, can then slide in both the X and Y direction as shown in FIG. 6D.

The teeth of the ratchet surface 15 are presented so that when the pawl 17 is engaged with the ratchet surface, the pawl will prevent the movement of the head rest support member 13 in the direction Z (being a direction where the head rest 9 is lowered). The ratchet surface however does allow for the movement of the head rest carrying member 13 in a direction Y opposite to direction Z without actively pressing the zone 18 to disengage the pawl 17 from the ratchet surface. This is as a result of the sloped surfaces of the ratchet surface. However it will be appreciated by a person skilled in the art that alternative surface configurations to the ratchet surface 15 may be provided to allow for an indexing to occur between the head rest carrying member 13 and the base pad 12. Such indexing may prevent movement in both directions in the absence of there being a pressing of the zone 18 to move the pawl 17. Indeed alternatively to the ratchet surface 15, a series of rebates may be provided in a surface of the head rest carrying member 13. These rebates may be square cut rebates into which a pawl can locate.

For the ratchet version in use a person can raise the head rest 9 without needing to push the zone 18. However the head rest cannot be moved downwards unless the zone 18 is pushed to disengage the pawl 17 from the ratchet surface. Therefore a person who rests their head on the head rest 9 without pushing the zone 18, will not displace the head rest 9 downwardly. To do so would require a pushing of the zone 18. The zone 18 is defined as part of the base pad 12 so as to be resiliently movable. Such resilient movement is to bias the pawl 17 towards a condition where it does engage the ratchet surface 15. Therefore a pushing of the zone 18 is in a direction opposite to the natural bias of the zone 18. However the most important direction in which the movement of the head support is prevented by some form of mechanism is in the downward direction. It is in the downward direction that the application of a force from the head of the user will be applied to the device and it is against this force that the elongate member must provide resistance so as to provide support to the head.

Figure 14:
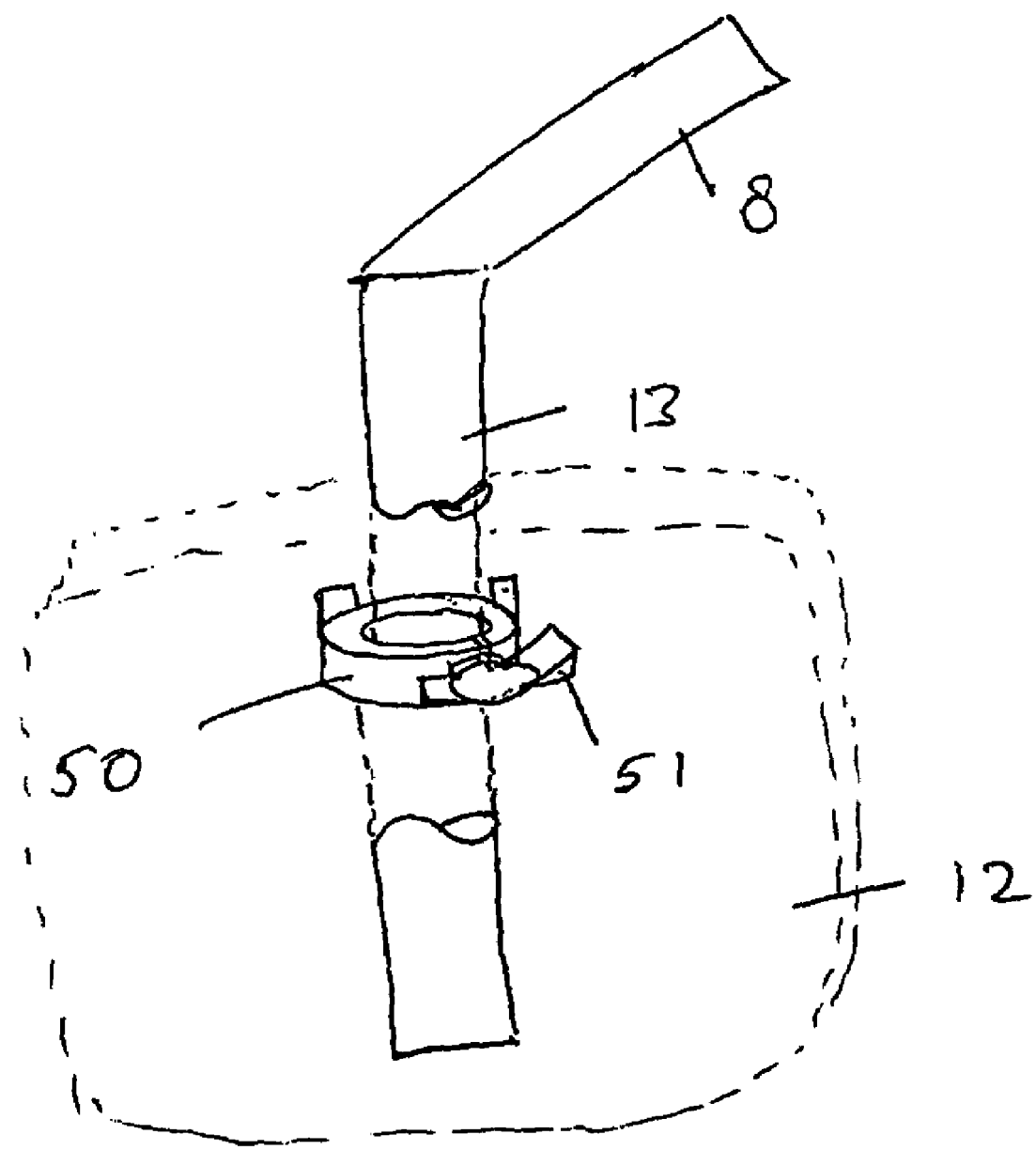
FIG. 14 shows a partial view of the device of the present invention showing a friction clamp which may be used to lock the device in place in regards to the vertically adjustable head rest aspect of the invention.

Alternative mechanisms for locking in place and prevent the movement of the elongate member 13 in at least one direction may include a friction clamp 50 as for example shown in FIG. 14. A friction clamp 50 may be engaged to the base pad and allow for the sliding therethrough of at least part of the elongate member 13. In the example shown in FIG. 14 the elongate member is of a circular cross section and the friction clamp 50 has a bore therethrough of a complimentary shape. The friction claim 50 is of a kind as commonly used on bicycles to lock a seat post of a bicycle relative to the frame of a bicycle. It includes a toggle handle 51 which can move to contract and dilate the bore through the friction clamp 50. In a contracted state the friction clamp will impart sufficient friction onto the elongate member 13 to lock it into position. In the most preferred form the mechanism for locking the movement of the elongate member 13 is of a quick release kind. Whilst it is envisaged that a threaded rod engagement or a rack and pinion engagement may also be used, such arrangements are disadvantageous in that it can take a significantly long time to displace the elongate member in the longitudinal direction by such alternative mechanisms.

Figure 7B:
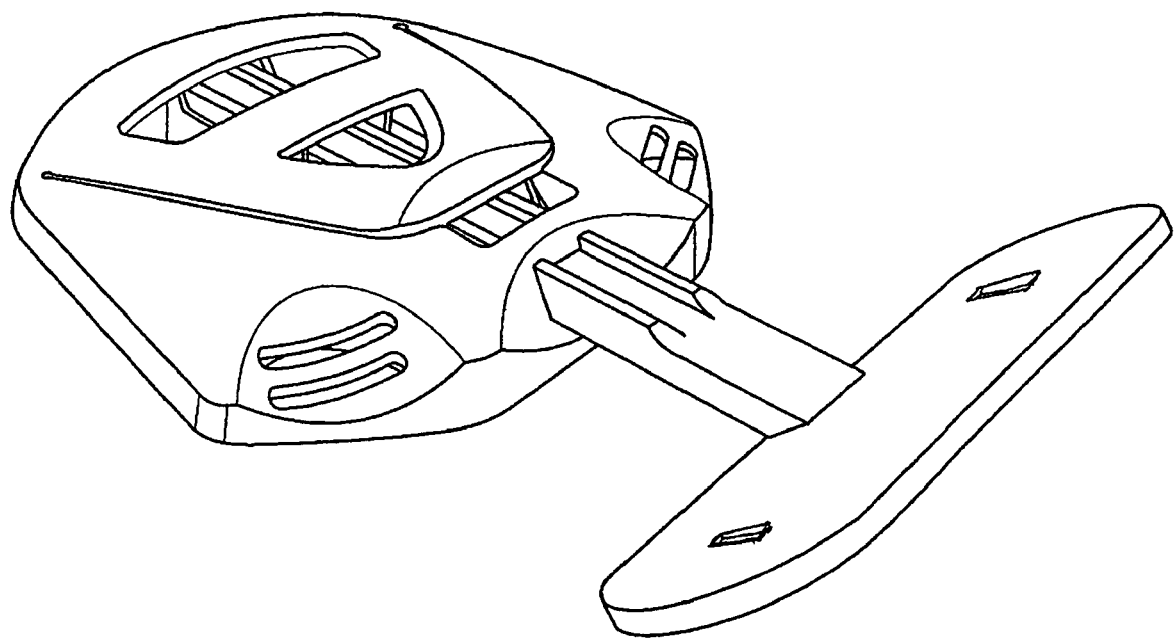
FIG. 7B is an alternative perspective view of FIG. 7A.
Figure 11:
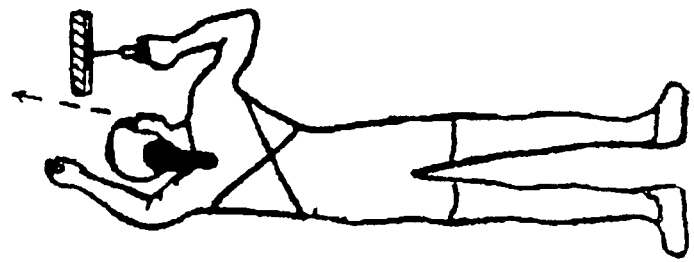
FIG. 11 illustrates the invention in use by, for example, a decorator or painter.
Figure 10:
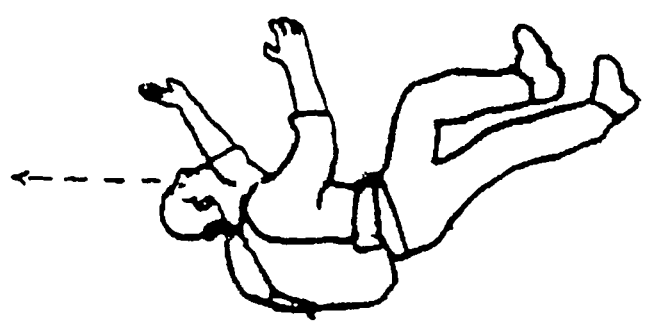
FIG. 10 illustrates the invention in use by, for example, a climber.
Figure 8:
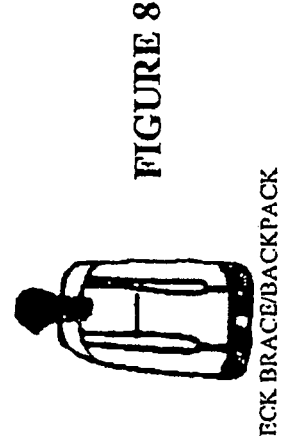
FIG. 8 illustrates a front view in the direction AA of FIG. 3 of an alternative form of the invention, being a back pack.
Figure 9:
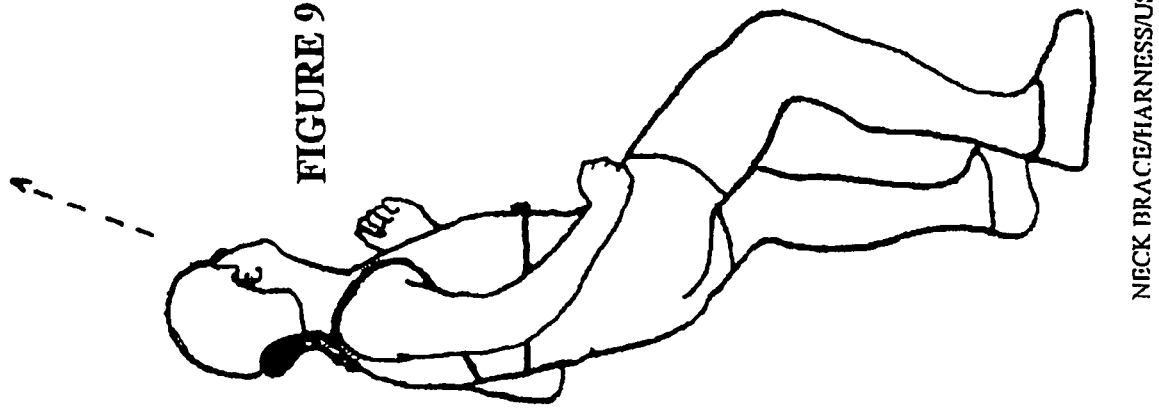
FIG. 9 illustrates the invention in use by, for example, a belayer.

The head support 1 as shown in FIGS. 6A-C and in FIGS. 7A and 7B, includes a head rest pad 10. The head rest pad 10 is engaged to an outwardly extending region 8 of the head rest carrying member 13. The outwardly extending region 8 of the head rest carrying member 13 extends outwardly from the body when the head support is in use. The elongate region of the head rest carrying member which is that portion slideably engaged with the base pad 12, extends substantially parallel to the body of the user (preferably parallel to the spine). The outwardly extending region 8 may in part form part of the head rest 9 or be entirely the head rest 9 of the rigid member 2. The outwardly extending region 8 presents a mount with which a pad 10 can be removeably engaged. The pad 10 may be made from a foam material to provide a certain degree of comfort to a user. The pad 10 may itself include a mounting base or substrate 23 to be contiguous with the outwardly extending region 8 at the head rest region 9 of the rigid member 2.

The substrate 23 and/or the outwardly extending region 8 may carry means to allow for the releasable engagement of the pad 10 with the outwardly extending region 8. With reference to FIGS. 6B and 6C, such means for engagement 24 are prongs which have clipping detail allowing for the prongs to be extended through apertures or into blind holes 25 of the rigid member 2. These apertures 25 can receive the prongs 24 and with the clipping detail of the prongs allow for the prongs to securely fasten the pad 10 to the outwardly extending region 8.

The prongs are preferably of a resiliently movable kind so that they can be moved to a condition to allow for the pad 10 to be disengaged from the outwardly extending region 8. The prongs may be made from a resilient plastics material. The apertures 24 are of a size to allow them to receive the prongs.

The ability for a convenient removal of the head rest pad 10 allows for the head rest pad 10 to be quickly and simply changed. Such change may be required due to the head rest pad 10 becoming dirty or for hygiene purposes or to allow for head rest pads of a different configuration to be presented for use. Head rest pads of different configurations may be necessary where the device of the present invention is used for different applications. In some applications not just vertical support but also support against the rotation of the head may be desired. In such cases a head rest pad which extends not just for engagement against the back of the head but also about part of the side of the head can be useful. As such interchangeable head rest pads may be provided at points of retail.

It will be appreciated by a person skilled in the art that many alternative forms of engagement of the head rest pad 10 with the outwardly extending region 8 can be provided. Such may also include the use of a hook and loop fastening mechanism or the clipping of the head rest pad in part about the outwardly extending region 8. Alternatively, adhesives or ties may be used. In a slight variation to the removable head rest pad as herein described, the head rest pad of the kind so far described (consisting largely of a foam pad) may remain affixed to the head support portion but where a removable sock or cover can be used to be contiguous the head rest pad and the head of the user. The cover is then, that portion in contact with the head of a wearer. The cover may be made from the likes of a tissue material and can be conveniently removed such as by having a perimeter elastic provided to locate about the head rest. The cover can be conveniently removed for the purposes of hygiene and cleanliness.

The head rest carrying member 13 of the rigid member 2 may also be included with bracing 26. A brace or braces 26 are preferably engaged with the head rest carrying member 13 and extends to have distal ends 27 engaged at the shoulder straps. The braces 26 may be removable from the device. The distal ends 27 may also have means for attachment at different locations of the shoulder straps 4. The purpose of the braces is to provide some resistance to the movement of the head rest outwardly away from the body.

The braces to provide bracing to the rigid member to prevent the head rest from moving outwardly away from the body of a user, are preferably engaged to the head rest carrying member 13 or to the head rest itself. Such engagement may be by a single brace passing through a fastening region of the head rest carrying member 13 (e.g. through a loop defined therein or an aperture defined therein) or alternatively the bracing may be of two pieces each piece extending in an opposite direction from the head rest carrying member 13. The bracing extends away from the head rest carrying member 13 in a direction towards the anterior of the body and is engaged to or engageable to the shoulder straps at an anterior more disposed portion of the head support. The extending of the bracing from the rigid member toward the anterior portion of the shoulder straps allows for the bracing to present a resistance to the movement of the head support in a direction parallel to a direction extending from the anterior to the posterior portion of the body (i.e. outwardly away from the body). The bracing also extends in a direction outwardly away from the head rest carrying portion 13 in a direction away from the centre line of the head rest carrying portion (i.e. along axis XX). Therefore the bracing can also provide some resistance to the movement of the head rest in or parallel to a plane which is parallel to the anterior and posterior planes of the body of a person.

The bracing is preferably adjustable in length so that a single head rest unit can be used by different people of different shapes and sizes as well as allowing for any adjustment of the unit to occur for a particular person for different uses that the device may be put. Such adjustment may be as a result of the bracing (preferably being webbing or straps or the like) having an adjustment feature or by having different anchor points to allow for it to be anchored at the shoulder straps. Alternatively the shoulder straps may present different anchor points to allow for the bracing to engage at different locations with the shoulder strap thereby allowing for different brace positions to be established.

A further aspect of the present invention is in relation to the location at where the chest band 11 of the harness is provided. It has been found that in order to assist in the preventing of the riding up of the rigid member that a chest band which extends about or proximate the waste of the torso of the user is not as effective as a band which extends immediately adjacent the pectorals of the rear of the user. A chest band 11 extending immediately below the pectoral muscles of the rear of a user aids and assists in the preventing of the riding up of the rigid member 2 when the device is in use.

Figure 13:
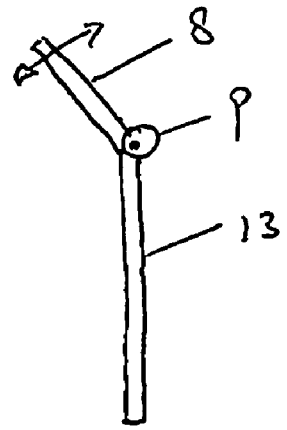
FIG. 13 is a side view of a head rest and elongate member wherein the head rest portion 8 and elongate member 13 are pivotable relative to each other about pivot P being of a rotational axis parallel to the anterior and posterior planes of the body of the wearer.

FIG. 13 is a side view of a head rest and elongate member wherein the head rest portion 8 and elongate member 13 are pivotable relative to each other about pivot P being of a rotational axis parallel to the anterior and posterior planes of the body of the wearer. The elongate member 13 engaged to the base pad or otherwise fixed to the harness is presented to remain relatively stationary to the body of the user whereas the projection 8 presenting the heat engageable region of the device is able to pivot relative to the elongate member 13. Such pivoting will allow for the head rest to be presented at different angles to facilitate the support of a head at different angles of inclination.

The invention claimed is:

1. A head support for supporting the head of a user when tilted backwards, said head support comprising
    a harness locatable to the upper body portions of a person,
    a rigid member extending from a region of said harness stabilized in respect of and by use of the harness relative to the body,
    wherein, when in use and said harness is attached to the body of a user, said rigid member extends rearwardly away from the harness and away from the user's body, out of alignment with and at an angle divergent from the harness to provide a support region thereof which when said person is in a substantially upright position, and their head is tilted backwards away from a stabilized straight ahead position to allow viewing of an object above the horizontal, said support region comes in contact with at least part of the back of the head and provides at least vertical support to only a posterior side of the user's head while also allowing complete forward movement of the head away from the rigid member to beyond the stabilized straight ahead position, and
    at least one bracing member, in use, extends from a point at or proximate said support region, between said rigid member and said harness to attach to said harness at a region proximate the posterior of said user's body to operationally brace said support region against movement thereof in a direction away from the body of the user.

2. The head support as claimed in claim 1 wherein said rigid member is or includes an elongate member having a vertically extending portion which, in use, extends substantially parallel with the spine of a user, and an outwardly projecting portion which extends in use, away from said vertically extending portion, outwardly from the body of a user, and said support region is provided at said outwardly projecting portion or near the distal end thereof.

3. The head support as claimed in claim 2 wherein said vertically extending portion is engaged to said harness.

4. The head support as claimed in claim 3 wherein said rigid member comprises a base member from which said elongate member projects, said elongate member engaged to said base member in a manner capable
    (a) to, in one condition of said rigid member, be displaceable relative to said base member to allow the movement of said support region in a direction along the longitudinal direction of said elongate member and
    (b) to, in a second condition of said rigid member, be selectively restrained from said movement relative to said base member by a securing mechanism.

5. The head support as claimed in claim 3 wherein said rigid member includes a base member from which said elongate member projects, said elongate member engaged, in a moveable manner in a direction along the longitudinal direction of said elongate member, to said base member and restrainable from movement in at least a direction wherein said support region displaces towards said base member, by a securing mechanism.

6. The head support as claimed in claim 5 wherein said elongate member is captured for sliding engagement to said base member to allow displacement of said elongate member relative to said base member in a direction along the longitudinal direction of said elongate member.

7. The head support as claimed in claim 5 wherein said securing mechanism is an indexed securing mechanism allowing retaining of said movement when said base member and said elongate member are at least two relative dispositions to each other.

8. The head support as claimed in claim 5 wherein said securing mechanism is a quick release clamp provided by said base member and in clampable engagement with said elongate member.

9. The head support as claimed in claim 3, wherein two bracing members extend from said elongate member to an anterior more to be disposed portion of said harness, each bracing member projecting from a respective side of said elongate member.

10. The head support as claimed in claim 3, wherein said bracing members are engaged to said elongate member at or proximate said support region.

11. The head support as claimed in claim 3, wherein said bracing members are straps.

12. The head support as claimed in claim 1 wherein said rigid member includes lateral extension, extending each side from said vertically extending portion of said rigid member, said lateral extension having at its laterally outward portions, a shoulder strap engaging formation to allow the location of shoulder straps of said harness with said lateral extension.

13. The head support as claimed in claim 12 wherein said lateral extension is a base member.

14. The head support as claimed in claim 1 wherein said support region is formed or shaped to additionally provide support to the sides of the head.

15. The head support as claimed in claim 1 wherein the head support includes one or more adjustment device selected from:
    (i) an adjustment device for altering a tilt of said support region;
    (ii) an adjustment device for altering a height of the support region with respect to the harness;
    (iii) an adjustment device for altering a distance between said rigid member and said back of said user.

16. The head support as claimed in claim 15 wherein said securing mechanism is defined by cooperative indexing elements of said elongate member and said base member.

17. The head support as claimed claim 1 wherein said support region includes padding to, in use, be rested on by the head of the user.

18. The head support as claimed in claim 17 wherein said cooperative indexing elements include an index surface and pawl, said index surface being part of one of said elongate element and said base element, and said pawi being part of the other of said elongate elements and said base.

19. The head support as claimed in claim 17 wherein said padding is provided by a removable pad, selectively fastenable to the support region.

20. The head support as claimed in claim 19 wherein said pawl can be selectively moved to a position where it is in a non operative association with said index surface to allow an unfettered movement of said elongate member with said base member.

21. The head support as claimed in claim 19 wherein said index surface is a ratchet surface comprising an array of saw tooth like projections.

22. The head support as claimed in claim 1 wherein said support region includes a cover to present a surface onto which the head of the user can rest.

23. The head support as claimed in claim 22 wherein said pawl is mounted in a manner biased towards a condition where it is in operative association with said index surface yet movable by a user to said position where it is in non operative association.

24. The head support as claimed in claim 22 wherein said cover is a removable cover.

25. The head support as claimed in claim 1 wherein said support region is presented to receive a head contact pad in a releasably fastenable manner, to hold said head contact pad in a position to allow it to engage with the head of the user.

26. The head support as claimed in claim 25 wherein said saw tooth like projections are presented in a manner to, when said pawl is in operative association, allow the movement of said elongate member in only one direction relative to said base member.

27. The head support as claimed in claim 1, wherein a plurality of bracing members, in use, extend in opposed directions between said rigid member to said harness to attach to said harness at a region adjacent the posterior of said user's body.

28. The head support as claimed in claim 1, wherein said harness includes over shoulders straps and each said bracing member is engaged to a respective over the shoulder strap.

29. The head support as claimed in claim 1, wherein said bracing members are adjusted to hold said elongate member in various anterior/posterior positions relative to the body of a user, when in use.

30. The head support as claimed in claim 1, wherein said bracing members include length adjustment elements to allow said bracing members to be adjusted.

31. The head support as claimed in claim 1, wherein one or more of each of said bracing members and said harness include a plurality of anchor points for engagement of said bracing element with said harness to allow said bracing members to be adjusted.

32. The head support as claimed in claim 1, wherein said harness includes over the shoulder straps and a chest strap engaged to said over the shoulder straps to be locatable about the chest of a wearer at or immediately below or adjacent the pectorals of a wearer.

33. The head support as claimed in claim 1, wherein said harness includes over the shoulder straps and a strap extending between the shoulder straps at the chest to restrain the over the shoulder straps from separating.

34. A head support comprising
a harness locatable to the upper body portions of a person,
a rigid member extending from a region of said harness stabilized in respect of and by the use of the harness relative to the body,
wherein, when in use, said harness is attached to the body of a person, said rigid member extends rearwardly away from the harness and away from the user's body, out of alignment with and at an angle divergent from the harness to provide a support region thereof which when said person is in a substantially upright position, and the head is tilted backwards away from a stabilized straight ahead position to allow viewing of an object above the horizontal, said support region comes in contact with at least part of the back of the head and provides at least vertical support to only a posterior side of said user's head while also allowing complete forward movement of the head away from the rigid member to beyond the stabilized straight ahead position, said rigid member being or including an elongate member having a vertically extending portion which, in use, extends substantially parallel with the spine of a user, and an outwardly projecting portion which extends in use, away from said vertically extending portion, outwardly from the body of a user, at said outwardly projecting portion or near the distal end thereof, said head support region being provided; and
at least one bracing member that, in use, extends from a point at or proximate said support region, between said rigid member and said harness to attach to said harness at a region proximate the posterior of said user's body to operationally brace said head support region against movement thereof in a direction away from the body of the user.

* * * * *

UNITED STATES PATENT AND TRADEMARK OFFICE
CERTIFICATE OF CORRECTION

| | |
|---|---|
| PATENT NO. | : 7,618,385 B2 |
| APPLICATION NO. | : 11/152784 |
| DATED | : November 17, 2009 |
| INVENTOR(S) | : Darrell Maitland Poole |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 920 days.

Signed and Sealed this

Nineteenth Day of October, 2010

David J. Kappos
*Director of the United States Patent and Trademark Office*